(12) United States Patent
Hashimoto et al.

(10) Patent No.: US 8,603,302 B2
(45) Date of Patent: Dec. 10, 2013

(54) PHOTOCATALYTIC MATERIAL, METHOD OF DECOMPOSING ORGANIC SUBSTANCE, INTERIOR MEMBER, AIR CLEANING DEVICE, AND DEVICE FOR PRODUCING OXIDIZING AGENT

(75) Inventors: Kazuhito Hashimoto, Tokyo (JP); Hiroshi Irie, Tokyo (JP); Huogen Yu, Tokyo (JP); Kazuhide Kamiya, Tokyo (JP); Koichi Takahama, Amagasaki (JP); Shinichiro Miki, Osaka (JP); Mitsuo Yaguchi, Ibaraki (JP)

(73) Assignees: The University of Tokyo, Tokyo (JP); Panasonic Corporation, Osaka (JP)

( * ) Notice: Subject to any disclaimer, the term of this patent is extended or adjusted under 35 U.S.C. 154(b) by 74 days.

(21) Appl. No.: 13/124,669

(22) PCT Filed: Oct. 29, 2009

(86) PCT No.: PCT/JP2009/068572
§ 371 (c)(1),
(2), (4) Date: Apr. 18, 2011

(87) PCT Pub. No.: WO2010/050548
PCT Pub. Date: May 6, 2010

(65) Prior Publication Data
US 2011/0198210 A1 Aug. 18, 2011

(30) Foreign Application Priority Data
Oct. 30, 2008 (JP) ................................ 2008-279828

(51) Int. Cl.
| | | |
|---|---|---|
| C07C 1/00 | (2006.01) | |
| C07C 2/00 | (2006.01) | |
| C07C 4/00 | (2006.01) | |
| C07C 5/00 | (2006.01) | |
| C07C 6/00 | (2006.01) | |
| B01J 23/70 | (2006.01) | |
| B01J 23/72 | (2006.01) | |
| B01J 23/00 | (2006.01) | |
| A62B 7/08 | (2006.01) | |
| C09D 1/00 | (2006.01) | |

(52) U.S. Cl.
USPC ...... 204/157.15; 502/345; 502/349; 422/120; 106/286.4

(58) Field of Classification Search
USPC ............ 502/338, 345, 350; 106/286.3, 286.4; 98/108; 422/120, 121, 186
See application file for complete search history.

(56) References Cited

U.S. PATENT DOCUMENTS 5,759,948 A * 6/1998 Takaoka et al. ............... 502/325
6,649,562 B2 * 11/2003 Naka et al. .................... 502/343

(Continued)

FOREIGN PATENT DOCUMENTS

JP 3601532 B2 10/2004

OTHER PUBLICATIONS

Chen et al., "Titanium Dioxide Nanomaterials: Synthesis, Properties, Modifications, and Applications" Chem. Rev. 2007, 107, 2891-2959.*

(Continued)

Primary Examiner — Anthony J Zimmer
(74) Attorney, Agent, or Firm — Renner, Otto, Boisselle & Sklar, LLP

(57) ABSTRACT

A divalent copper salt and/or trivalent iron salt is supported on a surface of a metal ion-doped titanium oxide obtained by doping titanium oxide with metal ions to give a metal ion-doped titanium oxide with a valence band potential of 3 V or more (vs. SHE, pH=0) and a bandgap of 3 V or less between the valence band and an energy level of electrons excited from the valence band (including conduction band minimum potential and isolated potential). The metal ion-doped titanium oxide can be made to exhibit strong oxidative decomposition activity when irradiated with visible light based on the fact the divalent copper salt or trivalent iron salt functions as a catalyst for multi-electron reduction of oxygen.

15 Claims, 1 Drawing Sheet

(56) References Cited

U.S. PATENT DOCUMENTS

| | | |
|---|---|---|
| 6,794,065 B1 | 9/2004 | Morikawa et al. |
| 2002/0169076 A1 | 11/2002 | Takeshi et al. |

OTHER PUBLICATIONS

Fan et al., "Preparation of Nano-TiO2 Doped with Cerium and Its Photocatalytic Activity," Journal of Rare Earths 24 (2006) 309-313.*

Larsson, Per-Olof et al., "Complete Oxidation of CO, Ethanol, and Ethyl Acetate over Copper Oxide Supported on Titania and Ceria Modified Titania". Journal of Catalysis, 1998, vol. 179, No. 1, pp. 72-89.

Li, Guangqin et al., "Different Effects of Cerium Ions Doping on Properties of Anatase and Rutile $TiO_2$", Applied Surface Science, 2006, vol. 253, No. 5, pp. 2481-2486.

Matsunaga, H. et al., "Preparation of M-dope $TiO_2$ (M=Ce, Ni) and its Photocatalytio Activity", 21st Fall Meeting of the Ceramic Society of Japan, 2008, p. 27.

Morikawa, Takeshi et al., "Visible-light-induced photocatalytic oxidation of carboxylic acids and aldehydes over N-doped $TiO_2$ loaded with Fe, Cu or Pt", Applied Catalysis B. Environmental, 2008, vol. 83, No. 1-2, pp. 56-62.

International Search Report for the Application No. PCT/JP2009/068572 mailed Jan. 12, 2010.

Teruhisa Ohno et al., "Sensitization of photocatalytic activity of S- or N-doped $TiO_2$ particles by adsorbing $Fe^{3+}$ cations", Applied Catalysis A: General, Jan. 19, 2006, vol. 302, Issue 1, p. 62-68.

* cited by examiner

PHOTOCATALYTIC MATERIAL, METHOD OF DECOMPOSING ORGANIC SUBSTANCE, INTERIOR MEMBER, AIR CLEANING DEVICE, AND DEVICE FOR PRODUCING OXIDIZING AGENT

TECHNICAL FIELD

The present invention relates to a photocatalytic material having visible light activity, to a method of decomposing an organic substance using this photocatalytic material, to an interior member formed using this photocatalytic material, to an air cleaning device, and to a device for producing an oxidizing agent.

BACKGROUND ART

Because they can oxidize and decompose organic materials and some inorganic materials such as nitrogen oxides using light, which is cheap and has an extremely low environmental impact, photocatalytic materials have been applied in recent years to environmental cleanup, deodorization, soil prevention, sterilization and other applications, and a variety of photocatalytic materials are being developed and studied.

Well-known photocatalysts include titanium oxide, which is responsive to ultraviolet radiation, but for use in residential interiors and other environments with little ultraviolet radiation there is a need for photocatalytic materials that are responsive to visible light, and these are being studied and developed.

For example, Patent Document 1 discloses a photocatalytic material having visible light activity, in which the oxygen atom sites of titanium oxide crystals are partially substituted with nitrogen atoms.

In the photocatalytic material disclosed in this Patent Document 1, visible light activity is achieved by the formation of a new isolated energy level on the negative side of the valence band of titanium oxide when the oxygen atom sites of the titanium oxides crystals are partially substituted with nitrogen atoms. When the electrons at the isolated level are exposed to photons having energy equal to or greater than the bandgap energy between the isolated level and the conduction band, they are excited to the conduction band of titanium oxide, while holes are created in the isolated level, resulting in visible light activity.

However, the isolated level formed in this way on the negative side of the valence band of titanium oxide has low potential, so the oxidative power of the holes resulting from photoexcitation of electrons by exposure to visible light is low, and the movement of holes produced at the isolated level is also restricted, so reactivity with the substrate to be oxidized is low. As a result, the problem with the photocatalytic material disclosed in Patent Document 1 has been that it has visible light activity but low oxidative decomposition activity.

Visible light absorption can also be achieved by doping the titanium ion sites of titanium oxide with another metal ion, thereby shifting the conduction band minimum potential of titanium oxide to the positive side or forming an isolated energy level on the positive potential side of the conduction band minimum potential. However, when the conduction band minimum potential of titanium oxide is shifted to the positive side sufficiently to provide visible light absorption, or when an isolated level is formed on the positive potential side of the conduction band minimum potential, the potential of the shifted conduction band minimum or resulting isolated level is larger than the one-electron reduction potential of oxygen (−0.046 V vs. SHE, pH=0), and the photoexcited electrons are no longer capable of one-electron reduction of oxygen. The photoexcited electrons recombine with the resulting holes and lose their oxidative decomposition activity, and because of this metal ion-doped titanium oxide has exhibited only very low oxidative decomposition activity.

Patent Document 1: Japanese Patent No. 3601532

DISCLOSURE OF THE INVENTION

In light of this, it is an object of the present invention to provide a metal ion-doped titanium oxide photocatalytic material exhibiting strong oxidative decomposition activity in response to visible light, as well as a method of decomposing an organic substance using this strong oxidative decomposition activity, an interior member, an air cleaning device and a device for producing an oxidizing agent.

In the photocatalytic material having visible light activity of the present invention, a divalent copper salt and/or trivalent iron salt is supported on a surface of a metal ion-doped titanium oxide obtained by doping titanium oxide with metal ions to give a metal ion-doped titanium oxide with a valence band potential of 3 V or more (vs. SHE, pH=0) and a bandgap of 3 V or less between the valence band and an energy level of electrons excited from the valence band (including conduction band minimum potential and isolated potential).

In order to control the valence band potential and bandgap in this way, either a conduction band minimum potential is shifted towards a positive potential or an isolated energy level is formed on a positive potential side of the conduction band minimum potential by doping the titanium oxide with metal ions, without changing the potential of the titanium oxide valence band.

The present invention exploits the fact that divalent copper salts and trivalent iron salts function as catalysts for multi-electron reduction of oxygen. That is, when a photocatalytic material formed by carrying a divalent copper salt or trivalent iron salt on the surface of a metal ion-doped titanium oxide is exposed to light having energy equal to or greater than the bandgap energy of the metal ion-doped titanium oxide, electrons photoexcited from the valence band of the metal ion-doped titanium oxide move from the conduction band of the metal ion-doped titanium oxide to the Cu (II) ions of the divalent copper salt or the Fe (III) ions of the trivalent iron salt supported on the metal ion-doped titanium oxide, reducing the Cu (II) ions to Cu (I) ions or the Fe (III) ions to Fe (II) ions. Then, as shown in the formulae below, the Cu (I) ions and Fe (II) ions perform multi-electron reduction of oxygen atoms in the environment, producing hydrogen peroxide in the case of 2-electron reduction or water in the case of 4-electron reduction, and restoring the Cu (II) and Fe (III) to their original states.

: 2-electron reduction $$2Cu(I)+O_2+2H^+ \rightarrow 2Cu(II)+H_2O_2$$

$$2Fe(II)+O_2+2H^+ \rightarrow 2Fe(III)+H_2O_2$$

: 4-electron reduction $$4Cu(I)+O_2+4H^+ \rightarrow 4Cu(II)+2H_2O$$

$$4Fe(II)+O_2+4H^+ \rightarrow 4Fe(III)+2H_2O$$

OR $$3Cu(I)+O_2+4H^+ \rightarrow 2Cu(II)+Cu(III)+2H_2O$$

$$4Fe(II)+O_2+2H_2O \rightarrow 4Fe(III)+4OH^-$$

In this way, the Cu (II) ions of the divalent copper salt or the Fe (III) ions of the trivalent iron salt supported on the metal ion-doped titanium oxide function as catalysts for multi-electron reduction of oxygen.

By this mechanism, because photoexcited electrons excited from the valence band of the metal ion-doped titanium oxide are efficiently consumed, producing water or hydrogen peroxide (an oxidizing species), the problem of low activity of the photoexcited electrons which has occurred with conventional metal ion-doped titanium oxides is resolved, and the photocatalytic material of the present invention provides oxidative decomposition activity with high efficiency in response to visible light.

Moreover, the potential of the valence band of the metal ion-doped titanium oxide is high, 3.0 V or more (vs. SHE, pH=0) as in the case of titanium oxide, and the holes produced in the valence band by light irradiation have the same strong oxidative power as holes produced in the valence band by exposure to ultraviolet light in ordinary photocatalytic titanium oxide. As a result, while in nitrogen-doped titanium oxide such as that disclosed in Patent Document 1 the holes produced in the isolated energy level have only weak oxidative power, the photocatalytic material of the present invention provides oxidative decomposition activity with high efficiency.

Another feature of the present invention is that a potential of the positively-shifted conduction band minimum or a potential of the isolated level formed on the positive side of the conduction band minimum potential is 0 V or more (vs. SHE, pH=0) but 0.8 V or less (vs. SHE, pH=0).

The reason why it is desirable for the positively-shifted conduction band minimum potential or the potential of the isolated level formed on the positive side of the conduction band minimum to be within this range is that this makes it easier for photoexcited electrons excited from the valence band of the metal ion-doped titanium oxide to move from the valence band of the metal ion-doped titanium oxide to the Cu (II) ions of the divalent copper salt and/or the Fe (III) ions of the trivalent iron salt supported on the metal ion-doped titanium oxide, given that the oxidation-reduction potential of Cu (I) and Cu (II) ions is 0.16 V (vs. SHE, pH=0) while the oxidation-reduction potential of Fe (II) and Fe (III) ions is 0.77 V (vs. SHE, pH=0).

Moreover, in the present invention, an amount of the divalent copper salt and/or trivalent iron salt supported on the metal ion-doped titanium oxide is preferably in a range of 0.0001 to 1% as a mass ratio of copper element and/or iron element to metal ion-doped titanium oxide.

If the supported amount of the divalent copper salt or trivalent iron salt is set within this range, the divalent copper salt or trivalent iron salt will be able to function adequately as a multi-electron reduction catalyst without blocking light irradiation of the metal ion-doped titanium oxide.

In the present invention, anions of the divalent copper salt or trivalent iron salt are preferable hydroxide ions. Good photocatalytic activity can be obtained with such hydroxide ions.

In the method of decomposing an organic substance of the present invention, the aforementioned photocatalytic material having visible light activity is exposed to visible light to decompose an organic substance.

As discussed above, the photocatalytic material of the present invention has strong oxidative decomposition activity when exposed to visible light, and can oxidatively decompose an organic substance with which it comes in contact.

The interior member of the present invention includes the aforementioned photocatalytic material having visible light activity in a surface layer, while the air cleaning device and device for producing an oxidizing agent of the present invention are formed using the aforementioned photocatalytic material having visible light activity.

When the photocatalytic material of the present invention is exposed to visible light having energy equal to or greater than the bandgap energy of the metal ion-doped titanium oxide, holes with strong oxidative power are produced, and hydrogen peroxide having oxidative power is also produced by means of the divalent copper salt or trivalent iron salt. Depending on the potential of the positively-shifted conduction band or the potential of the isolated level formed on the positive side of the conduction band minimum, the absorption wavelength end of the metal ion-doped titanium oxide is about 450 nm, while the absorption wavelength end of ordinary photocatalytic titanium oxide is about 400 nm. Because the white fluorescent lamps commonly used in interiors have strong luminance at about 400 to 450 nm, the photocatalytic material of the present invention can provide strong oxidative decomposition activity in response to visible light at these wavelengths in interior environments for example, something that is not provided by conventional titanium oxide photocatalysts.

Because the conductive band minimum potential of the titanium oxide is so small in conventional titanium oxide photocatalysts, oxygen in the environment undergoes one-electron reduction, producing superoxide anions ($.O_2^-$), which are an active oxygen species.

: One-electron reduction

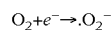

$$O_2 + e^- \rightarrow .O_2^-$$

However, in the photocatalytic material of the present invention the photoexcited electrons that are excited by exposure to visible light are consumed by multi-electron reduction of, oxygen via the Cu (II) ions or Fe (III) ions, producing hydrogen peroxide or water as discussed above. Thus, from a safety standpoint the photocatalytic material of the present invention has the advantage of not producing superoxide anions, which are an active oxygen species.

That is, the photocatalytic material of the present invention has the advantages of exhibiting strong oxidative decomposition activity in response to visible light, and not producing superoxide anions, which are a harmful active oxygen species. This means that it has the properties of visible light activity and safety that are especially valued when photocatalytic materials are used in interior members in residences, and the photocatalytic material of the present invention is especially suited to use in interior members in residences. In other words, a residential interior member formed with a surface layer of the photocatalytic material of the present invention has strong visible light activity and safety.

Because it exhibits strong oxidative decomposition activity in response to visible light, moreover, the photocatalytic material of the present invention is suited to use in air cleaning devices. That is, in air cleaning devices using conventional titanium oxide and other catalysts, the catalyst must be activated using an expensive UV light sources, but with the photocatalytic material of the present invention it is possible to prepare an inexpensive air cleaning device because strong oxidative decomposition activity can be achieved using a cheap fluorescent light source.

Moreover, the photocatalytic material of the present invention produces hydrogen peroxide as discussed above when exposed to visible light. Hydrogen peroxide is a stable oxidizing agent, and because it is also relatively long-lived, it has the potential to retain the oxidative decomposition activity of the photocatalyst of the present invention for some time after the end of light exposure. In addition, if the hydrogen peroxide thus produced could be transported via a suitable medium, the oxidative decomposition activity could be used at a location other than the surface of the photocatalytic material of the present invention. Consequently, a stable and long-lived oxidizing agent can be produced if a device for producing an oxidizing agent is formed using the photocatalytic material of the present invention.

The present invention provides a metal ion-doped titanium oxide photocatalytic material that exhibits strong oxidative decomposition activity when exposed to visible light.

A method of decomposing an organic substance, an interior member, an air cleaning device and a device for producing an oxidizing agent can also be provided that make use of this strong oxidative decomposition activity.

BEST MODE FOR CARRYING OUT THE INVENTION

Figure 1:
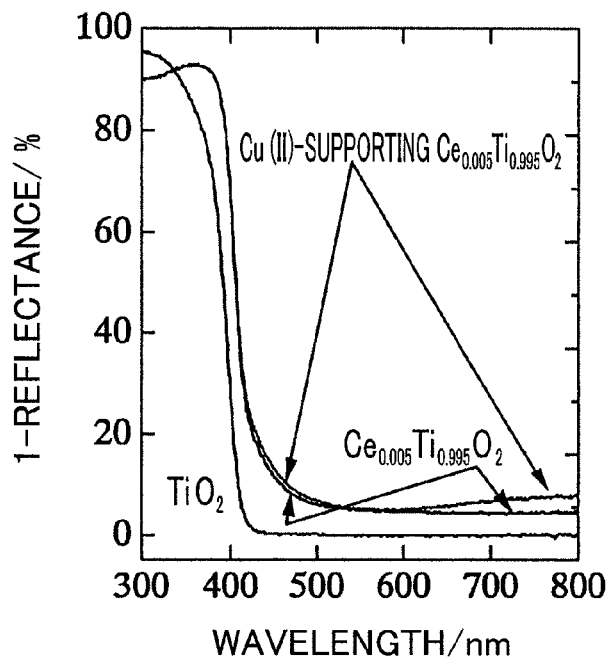
FIG. 1 is a graph showing the UV-visible diffuse reflectance spectra.

The best mode for carrying out the present invention is explained below.

The titanium oxide in the present invention is not particularly limited, and fine particle titanium oxide or thin-film titanium oxide can be used. Fine particles are especially desirable because a large specific surface area of the photocatalyst is advantageous in photocatalytic reactions. The crystal structure of the titanium oxide is also not particularly limited, and may be rutile, anatase, brookite or the like.

The present invention uses metal ion-doped titanium oxide, which is titanium oxide doped with metal ions. The metal ions used for doping the titanium oxide are not particularly limited so long as they yield a valence band potential of 3 V or more (vs. SHE, pH=0) and a bandgap of 3 V or less between the valence band and the energy level of electrons excited from the valence band, specifically by shifting the conduction band minimum potential of the titanium oxide to the positive side or by forming an isolated level on the positive potential side of the conduction band minimum, but examples include Ce (IV), Ge (IV), V (V), Ga (III) and the like. The higher the potential of the valence band, the greater the oxidizing power of the holes produced in the valence band, but if the potential is too high the bandgap will spread and visible light absorption will be lost, so about 3 to 3.3 V (equivalent to titanium oxide) is desirable. The smaller the bandgap, the more the wavelength of absorbable light will shift towards longer wavelengths, expanding the effective wavelength range, but the size of the bandgap is also restricted by the desirable range of potential between the valence band and the positively-shifted conduction band minimum potential or the potential of the isolated level formed on the positive side of the conduction band minimum in the metal ion-doped titanium oxide, and is therefore preferably in the range of 2.2 to 3 V.

The method of manufacturing the metal ion-doped titanium oxide by doping titanium oxide with metal ions is not particularly limited, and a sol-gel method, solid-phase method, hydrothermal method, or lamination method using sputtering or CVD can be used.

The photocatalytic material of the present invention can then be obtained by supporting a divalent copper salt and/or trivalent iron salt on the surface of the metal ion-doped titanium oxide. Either a divalent copper salt or a trivalent iron salt may be supported, or both a divalent copper salt and a trivalent ion salt may be supported.

The method of supporting the divalent copper salt or trivalent iron salt on the metal ion-doped titanium oxide is not particularly limited, and aqueous solution impregnation may be used for example.

In the present invention, the divalent copper salt or trivalent iron salt is not particularly limited, and for example cupric chloride ($CuCl_2.2H_2O$), ferric chloride ($FeCl_3$) or the like can be used as the starting material for the divalent copper salt or trivalent iron salt.

Of these, an anion of the divalent copper salt or trivalent iron salt is preferable a hydroxide ion. This is because the photocatalytic activity may be less with other ion species. As the starting material, cupric chloride ($CuCl_2.2H_2O$) can be used in the case of a divalent copper salt and ferric chloride ($FeCl_3$) can be used in the case of a trivalent iron salt, and when the photocatalytic material of the present invention is produced, the anions are converted to hydroxide ions as the divalent copper salt or trivalent iron salt becomes supported in the form of highly dispersed fine particles on the surface of the metal ion-doped titanium oxide by means of a process of heating and impregnating the metal ion-doped titanium oxide in an aqueous solution. Cu (II) is presumed to be in a six-coordinate state, and the specific divalent copper salt is presumed to be Ti—O—$Cu(OH)_2.3H_2O$ for example when bound to the oxygen atoms of the metal ion-doped titanium oxide, or $Cu(OH)_2.4H_2O$ for example when adsorbed.

The amount of the divalent copper salt or trivalent iron salt that is supported on the metal ion-doped titanium oxide is preferably such that the amount of the copper element in the divalent copper salt or the iron element in the trivalent iron salt is within the range of 0.0001 to 1% as a mass percentage of the metal ion-doped titanium oxide. When a divalent copper salt and trivalent iron salt are each supported independently, it is set so that the copper element in the divalent copper salt is within the range of 0.0001 to 1% and the iron element in the trivalent iron salt is within the range of 0.0001 to 1%, while if both a divalent copper salt and trivalent iron salt are supported, it is set so that the total of the copper element in the divalent copper salt and the iron element in the trivalent iron salt is within the range of 0.0001 to 1%.

In the photocatalytic material of the present invention, since it is the metal ion-doped titanium oxide that is photoexcited, photocatalytic activity may be reduced if light irradiation of the metal ion-doped titanium oxide is blocked when the metal ion-doped titanium oxide is broadly covered with a divalent copper salt or trivalent iron salt. Moreover, because the divalent copper salt or trivalent iron salt functions as a catalyst for multi-electron reduction of oxygen, it is preferably supported on the metal ion-doped titanium oxide in the form of highly-dispersed fine particles rather than being aggregated, in order to achieve higher catalytic efficiency. For these reasons, the supported amount of the divalent copper salt or trivalent iron salt is preferably such that the amount of the copper element or iron element is 1% or less as a mass percentage of the metal ion-doped titanium oxide. Conversely, if too little divalent copper salt or trivalent iron salt is supported it will not function adequately as a multi-electron reduction catalyst, so the amount of the copper element or iron element is preferably 0.0001% or more as a mass percentage of the metal ion-doped titanium oxide.

As discussed above, when a photocatalytic material of the present invention obtained in this way is exposed to visible light having energy equal to or greater than the bandgap of the metal ion-doped titanium oxide, holes with strong oxidizing power are produced and hydrogen peroxide is also produced by means of the divalent copper salt or trivalent iron salt, and both of these can be used to oxidatively decompose an organic material. The absorption wavelength edge of the metal ion-doped titanium oxide is about 450 nm, and since the white fluorescent lamps commonly used in interiors have strong luminance at about 400 to 450 nm, the photocatalytic material of the present invention can be used to provide strong oxidative decomposition activity under visible light in interior environments for example.

The organic material that is decomposed by the photocatalytic material of the present invention is not particularly limited, and examples include ketones and aldehydes such as acetaldehyde and formaldehyde (a cause of "sick house syndrome"), as well as toluene and other volatile organic compounds (VOCs). Other organic materials that can be oxidatively decomposed include methyl mercaptane, trimethylamine and other odoriferous materials, sebum, soap residue, grease, flavorings and other contaminants, and *E. coli*, *Staphylococcus aureus* and other bacteria and the like. Thus, the photocatalytic material of the present invention has the functions of environmental cleanup, deodorization, soil prevention, sterilization and the like, and can be used for applications requiring these functions.

There are no particular limits on the members, equipment and the like in which the photocatalytic material of the present invention can be used. The photocatalytic material of the present invention has excellent oxidative decomposition activity in response to ultraviolet light as well as visible light, and can also be used favorably in applications for which existing photocatalytic materials are used. Of these, application to interior members and air cleaning devices is preferred.

As discussed above, the photocatalytic material of the present invention has the properties of exhibiting strong oxidative decomposition activity in response to visible light, and not producing superoxide anions, which are a harmful active oxygen species. The properties are especially valued for photocatalytic materials used in interior members in residences, so the photocatalytic material of the present invention is especially applicable to interior members used in residences.

Application to interior members can be accomplished by including the photocatalytic material of the present invention in the surface layer of an interior member. The method of including the photocatalytic material in the surface layer of an interior member is not particularly limited, and for example the photocatalytic material may be compounded with a coating material, and this coating material can be coated on the surface of the interior member to thereby form a surface layer containing the photocatalytic material.

Specific examples of interior members containing the photocatalytic material of the present invention in the surface layer are not particularly limited, but may include doors, cupboard doors, ceiling materials, wall materials, floor materials, partitions, fixtures, stairs, railings, banisters, window frames, sinks, and kitchen, lavatory and bath fixtures and the like.

Since the photocatalytic material of the present invention exhibits strong oxidative decomposition activity in response to visible light as discussed above, it is also applicable to air cleaning devices. That is, in air cleaning devices using conventional titanium oxide and other photocatalysts, the catalyst must be activated with an expensive UV light source, but with the photocatalytic material of the present invention it is possible to prepare an inexpensive air cleaning device because strong oxidative decomposition activity can be achieved using a cheap fluorescent light source.

The method of using the photocatalytic material of the present invention in an air cleaning device is not particularly limited, but for example the photocatalytic material can be carried on an air filter that is incorporated into an air cleaning device.

Another feature of the photocatalytic material of the present invention is that it produces hydrogen peroxide when exposed to visible light. Hydrogen peroxide is a stable oxidizing agent, and since it also has a relatively long life, it has the potential to retain the oxidative decomposition activity of the photocatalyst of the present invention for some time after the end of light exposure. In addition, if the hydrogen peroxide thus produced could be transported via a suitable medium, the oxidative decomposition activity could be used at a location other than the surface of the photocatalytic material of the present invention. Thus, the photocatalytic material of the present invention can also be applied to a device for producing an oxidizing agent.

The method of using the photocatalytic material of the present invention as a device for producing an oxidizing agent is not particularly limited, but one example is a method of manufacturing a device for producing an oxidizing agent equipped with a light source and a member with the photocatalytic material of the present invention supported thereon. This device for producing an oxidizing agent could be incorporated into a washing machine, which would produce hydrogen peroxide inside the washing machine using water as the medium for hydrogen peroxide, and soil and odors inside the washing machine would then be oxidatively decomposed by the hydrogen peroxide.

EXAMPLES

Next, the present invention is explained in detail by means of examples. The present invention is not limited to these examples, however.

Example 1

Titanium oxide ($TiO_2$) powder (rutile, Tayca) and cerium oxide ($CeO_2$, Wako Pure Chemical Industries, Ltd.) were mixed at a molar ratio of 0.995:0.005, and baked for 5 hours at 1200° C. to obtain cerium ion-doped titanium oxide. The valence band maximum potential of this cerium ion-doped titanium oxide was 3 V (vs. SHE, pH=0) as measured by ultraviolet photoelectron spectroscopy. The valence band minimum potential was 0.05 V (vs. SHE, pH=0) as measured by flat band potential measurement.

This cerium ion-doped titanium oxide was then suspended and dispersed in distilled water so that the ratio of $TiO_2$ to distilled water was 10 mass %. Next, $CuCl_2 \cdot 2H_2O$ (Wako Pure Chemical Industries, Ltd.) was added so that the ratio of Cu (II) to $TiO_2$ was 0.1 mass %, and the mixture was heated with agitation to 90° C. and maintained at that temperature for 1 hour. The resulting suspension was filtered by suction filtration, and the residue was washed with distilled water and heat dried at 110° C. to obtain a cerium ion-doped titanium oxide with a supported divalent copper salt as a sample for evaluation.

When this Cu (II)-supporting cerium ion-doped titanium oxide with supported divalent copper salt was subjected to inductively-coupled plasma emission spectrometry and atomic absorption analysis, 0.03 mass % (vs. $TiO_2$) of Cu (II) was found to be supported.

FIG. 1 shows the UV-visible diffuse reflectance spectra of titanium oxide ($TiO_2$), cerium ion-doped titanium oxide ($Ce_{0.005}Ti_{0.995}O_2$) and Cu (II)-supporting cerium ion-doped titanium oxide. It can be seen from FIG. 1 that the bandgap is narrowed and the absorption wavelength end is shifted to a longer wavelength by means of cerium ion doping.

Example 2

Cerium ion-doped titanium oxide was obtained as in Example 1. This cerium ion-doped titanium oxide was then suspended and dispersed in distilled water so that the ratio of $TiO_2$ to distilled water was 10 mass %. $FeCl_3 \cdot 2H_2O$ (Wako Pure Chemical Industries, Ltd.) was then added so that the ratio of Fe (III) to $TiO_2$ was 0.1 mass %, and the mixture was heated with agitation to 90° C. and maintained at that temperature for 1 hour. The resulting suspension was filtered by suction filtration, and the residue was washed with distilled water and heat dried at 110° C. to obtain cerium ion-doped titanium oxide with a supported trivalent ion salt as a sample for evaluation.

When this Fe (III)-supporting cerium ion-doped titanium oxide with supported trivalent iron salt was subjected to inductively-coupled plasma emission spectrometry and atomic absorption analysis, 0.02 mass % (vs. $TiO_2$)Fe (III) was found to be supported.

Comparative Example 1

Anatase-type titanium oxide (ST-01, Ishihara Sangyo Kaisha Ltd.) was used as the evaluation sample.

Comparative Example 2

Anatase-type titanium oxide (ST-01, Ishihara Sangyo Kaisha Ltd.) was annealed for 3 hours at 550° C. in an ammonia gas flow (1 SCCM) to obtain nitrogen-doped titanium oxide as a sample for evaluation.

(Property Evaluation)

The photocatalytic activity of the evaluation samples of Examples 1 and 2 and Comparative Examples 1 and 2 above was evaluated by assaying the concentrations of acetone and $CO_2$ produced as a result of vapor-phase oxidative decomposition of 2-propanol (IPA) by exposure to visible light. The details are given below.

First, 300 mg of each evaluation sample was spread uniformly on a Petri dish (area 5.51 cm$^2$) having an inner diameter of 26.5 mm, and this was enclosed in a 500 ml quartz vessel. Synthetic air was supplied to the vessel, which was then exposed to an all-optic Xe lamp (Luminar Ace 251, Hayashi Watch-Works Co., Ltd.) to decompose residual organic substances on the surface of the evaluation sample. Once $CO_2$ emission from the residual organic substances was confirmed to have ended, synthetic air was once again supplied inside the vessel.

Meanwhile, reactive IPA gas was passed through dry nitrogen gas, and then collected as vaporized IPA inside a tedra pack. The equivalent of 300 ppmv (6.1 µmol) of the collected IPA was introduced into a vessel supplied with synthetic air. This vessel was then left in a dark place, the degree to which the introduced IPA was adsorbed on the surface was observed for 10 hours or more, and absorption equilibrium was confirmed. After absorption equilibrium had been confirmed, the vessel was irradiated from the top with a Xe lamp as the light source with the irradiating light wavelength range controlled at 400 to 530 nm by means of glass filters (L-42, B47, C-40C, AGC Techno Glass Co., Ltd.). The gas inside the vessel was then sampled at fixed intervals during irradiation, and IPA and its decomposition products acetone and $CO_2$ were assayed with a hydrogen flame ionization gas chromatograph (GC-8A, Shimadzu Corporation). However, the $CO_2$ was assayed via a methanizer (MT-N, Shimadzu Corporation), which methanizes using a metal Ni catalyst in a flow of hydrogen. The intensity of the irradiating light was measured for each wavelength with a spectral irradiance illuminance meter (USR-30V, Ushio Inc.), and adjusted to $1.00 \times 10^3$ mWcm$^{-2}$. The number of photons absorbed per unit time (absorbed photons) was determined by multiplying the irradiated area (Petri dish area 5.51 cm$^2$) times the absorbed ratio (1-reflectance), which was determined using the diffuse radiation spectrum of each evaluation sample. The $CO_e$ production rate was determined by the least-square method, and the quantum yield QE was determined by the following formula.

$QE = 6 \times CO_2$ production rate/absorbed photons

Figure 2:
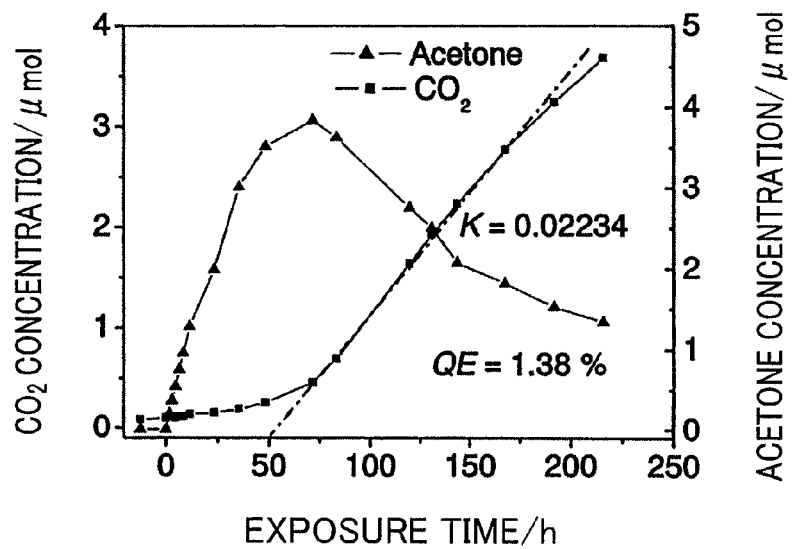
FIG. 2 is a graph showing the results of IPA analysis in Example 1.

FIG. 2 shows one example of IPA decomposition results for Cu (II)-supporting cerium ion-doped titanium oxide in Example 1. Table 1 shows the QE values from the evaluation results for Examples 1 and 2 and Comparative Examples 1 and 2. In Comparative Example 1, "N.D." means below the detection limit.

TABLE 1

|  | Example 1 | Example 2 | Comparative Example 1 | Comparative Example 2 |
|---|---|---|---|---|
| Quantum yield QE | 1.38% | 1.12% | N.D. | 0.08% |

As shown in FIG. 2, an increase in $CO_2$ production attributable to acetone production and acetone reduction is seen in Example 1, confirming the presence of visible light activity. Also, as shown in Table 1, quantum yield QE is high in Examples 1 and 2, confirming an increase in light use efficiency.

The invention claimed is:

1. A photocatalytic material having visible light activity, wherein a divalent copper salt is supported on a surface of a metal ion-doped titanium oxide obtained by doping titanium oxide with metal ions to give a metal ion-doped titanium oxide with a valence band potential of 3 V or more vs. SHE, pH=0, and a bandgap of 3 V or less between the valence band and an energy level of electrons excited from the valence band including conduction band minimum potential and isolated potential, wherein anions of the divalent copper salt are hydroxide ions.

2. The photocatalytic material having visible light activity according to claim 1, wherein a divalent copper salt is supported on a surface of metal ion-doped titanium oxide in which a conduction band minimum potential is shifted towards a positive potential or an isolated energy level is formed on a positive potential side of the conduction band minimum potential by doping the titanium oxide with metal ions.

3. The photocatalytic material having visible light activity according to claim 1, wherein an amount of the divalent copper salt supported on the metal ion-doped titanium oxide is in a range of 0.0001% to 1% as a mass ratio of copper element to metal ion-doped titanium oxide.

4. The photocatalytic material baying visible light activity according to claim 1, wherein a potential of a positively-shifted conduction band minimum or a potential of an isolated energy level formed on the positive potential side of the conduction band minimum of the metal ion-doped titanium oxide is 0 V or more vs. SHE, pH=0 but 0.8 V or less vs. SHE, pH=0.

5. A method of decomposing an organic substance by exposing the photocatalytic material having visible light activity according to claim 1 to visible light to decompose an organic substance.

6. An interior member comprising a photocatalytic material having visible light activity according to claim 1 in a surface layer.

7. An air cleaning device comprising the photocatalytic material having visible light activity according to claim 1.

8. A device for producing an oxidizing agent, comprising the photocatalytic material having visible light activity according to claim 1.

9. The photocatalytic material having visible, light activity according to claim 2, wherein an amount of the divalent, copper salt supported on the metal ion-doped titanium oxide is in a range of 0.0001% to 1% as a mass ratio of copper element to metal ion-doped titanium oxide.

10. The photocatalytic material having visible light activity according to claim 2, wherein a potential of the positively-shifted conduction band minimum or a potential of the isolated energy level formed on the positive potential side of the conduction band minimum of the metal ion-doped titanium oxide is 0 V or more vs. SHE, pH=0 but 0.8 V or less vs. SHE, pH=0.

11. The photocatalytic material haying visible light activity according to claim 3, wherein a potential of a positively-shifted conduction band minimum or a potential of an isolated energy level formed on the positive potential side of the conduction band minimum of the metal ion-doped titanium oxide is 0 V or more vs. SHE, pH=0 but 0.8 V or less vs. SHE, pH=0.

12. A method of decomposing an organic substance by exposing the photocatalytic material having visible light activity according to claim 2 to visible light to decompose an organic substance.

13. A method of decomposing an organic substance by exposing the photocatalytic material having visible light activity according to claim 3 to visible light to decompose an organic substance.

14. A method of decomposing an organic substance by exposing the photocatalytic material having visible light activity according to claim 4 to visible light decompose an organic substance.

15. An interior member comprising a photocatalytic material having visible light activity according to claim 2 in a surface layer.

* * * * *